(12) United States Patent
Smith

(10) Patent No.: US 11,564,940 B2
(45) Date of Patent: *Jan. 31, 2023

(54) TRACE ELEMENT SOLUTION

(71) Applicant: WARBURTON TECHNOLOGY LIMITED, Dublin (IE)

(72) Inventor: William Alfred Smith, Dublin (IE)

(73) Assignee: WARBURTON TECHNOLOGY LIMITED, Dublin (IE)

( * ) Notice: Subject to any disclaimer, the term of this patent is extended or adjusted under 35 U.S.C. 154(b) by 79 days.

This patent is subject to a terminal disclaimer.

(21) Appl. No.: 17/069,238

(22) Filed: Oct. 13, 2020

(65) Prior Publication Data

US 2021/0093664 A1    Apr. 1, 2021

Related U.S. Application Data

(63) Continuation of application No. 15/767,002, filed as application No. PCT/IB2015/057726 on Oct. 9, 2015, now Pat. No. 10,799,531.

(51) Int. Cl.

| | | |
|---|---|---|
| *A61K 33/34* | (2006.01) | |
| *A61K 33/04* | (2006.01) | |
| *A61K 33/30* | (2006.01) | |
| *A61K 33/32* | (2006.01) | |
| *A61K 9/00* | (2006.01) | |
| *A61K 9/08* | (2006.01) | |
| *A61K 33/18* | (2006.01) | |
| *A61K 47/18* | (2017.01) | |

(52) U.S. Cl.
CPC ............ *A61K 33/34* (2013.01); *A61K 9/0019* (2013.01); *A61K 9/08* (2013.01); *A61K 33/04* (2013.01); *A61K 33/18* (2013.01); *A61K 33/30* (2013.01); *A61K 33/32* (2013.01); *A61K 47/183* (2013.01); *A61K 2300/00* (2013.01)

(58) Field of Classification Search
CPC ........ A61K 33/34; A61K 9/0019; A61K 9/08; A61K 33/04; A61K 33/18; A61K 33/30; A61K 33/32; A61K 47/183; A61K 2300/00

See application file for complete search history.

*Primary Examiner* — Snigdha Maewall

(74) *Attorney, Agent, or Firm* — Stephen J. Weyer, Esq.; Stites & Harbison, PLLC

(57) ABSTRACT

A trace element solution comprises at least the following metals zinc directly and/or indirectly from Zn-EDTA and/or Zn oxide; manganese directly and/or indirectly from Mn-EDTA and/or manganese carbonate; copper directly and/or indirectly from Cu-EDTA and/or copper oxide and/or copper sulphate, and/or copper carbonate; selenium derived directly and/or indirectly from $Na_2SeO_4$ and/or $Na_2SeO_3$. The metals are present in a solution of water, chlorocresol and/or benzyl alcohol, at a concentration of metals of at least 95 mg/ml. The pH of the trace element solution adjusted by means of 30% NaOH in an injectable trace element solution that is visually stable.

9 Claims, No Drawings

TRACE ELEMENT SOLUTION

CROSS-REFERENCE TO RELATED PATENT

This is a continuation of U.S. Pat. No. 10,799,531 granted from U.S. patent application Ser. No. 15/767,002 filed Apr. 9, 2018 as a 371 application of PCT/IB2015/057726 filed Oct. 9, 2015, all herein incorporated by reference.

FIELD OF INVENTION

The present invention relates to a trace element solution.
More particularly, the present invention relates to a trace element solution incorporating Zinc, Manganese, Copper and Selenium.

BACKGROUND TO INVENTION

It has been found that there is a deficiency of certain trace elements in pastures for livestock in particular areas around the world. Various suggestions have been made to provide the required trace elements to such animals. Different chemical compounds and complexes have been investigated for applying the trace elements by way of licks, drenches or injections.

In general the problem with injectable solutions is that the concentrations of the minerals in the solutions is too low. This means that relatively large quantities have to be injected, which in turn causes tissue damage and also abscesses at the site of injection. Furthermore, it is generally the case that different trace elements are seldomly individually sufficient. This means that two or more trace element solutions have to be provided by way of separate injections.

ZA 1982/6778 (Laurie) discloses a trace element solution and a method of providing the trace elements to livestock. These trace element solutions include ethylene diamine tetra acetic acid complex of the required mineral in suitable quantities. However, the trace element solution includes no selenium or selenite compound.

In the specification and claims the expression EDTA refers to ethylene diamine tetraacetic acid ($C_{10}H_{16}O_8N_2$ or ($HO_2CH_2C)_2NCH_2CH_2N$—$(CH_2CO_2H)_2$).

U.S. Pat. No. 4,335,116 (Howard) discloses mineral-containing therapeutic compositions containing EDTA complexes of trace elements. Notably, U.S. Pat. No. 4,335,116 utilises tetra-sodium EDTA, a selenium glycine complex, and metal chlorides for the preparation of the EDTA complexes. Unfortunately, the chloride ions cause contamination and each complex solution has to be made individually. Furthermore, overnight time is required for complexing and heating up afterward to speed up the process, requiring extra apparatus. If mixtures are required, the individual solutions are to be blended. If various concentrations as well as compositions are to be made, it can only be done in a cumbersome way, requiring extra apparatus. A further problem arises when mixtures of high concentration are needed. In certain cases it would be impossible to deliver them, because mixing is always accompanied by dilution. The maximum concentration achieved with this method was 13,5 mg/ml.

U.S. Pat. No. 6,638,539 (Laurie et al) discloses a method of preparing a trace element solution, which includes the steps of providing at least one EDTA-complex, of providing a sodium selenite solution, and of combining the EDTA-complexes and the sodium selenite solution. However, the method enables production of a trace element solution of only about 55 mg/ml.

U.S. Pat. No. 7,285,292 (Laurie et al) discloses a trace element solution, which comprises at least one metal selected from the group comprising selenium, copper, zinc, manganese and chromium and which comprises a concentration of the metal(s) of at least 60 mg/ml. The solution further comprises at least one compound selected from the group comprising iodine, potassium iodide, sodium iodide, iron, iron chloride, zinc oxide, manganese sulphate, sodium selenite, copper carbonate, sodium carbonate, anhydrous disodium EDTA and sodium hydroxide. The trace element solution is prepared by a method consisting essentially of the steps of preparing a $MnCO_3$ mixture in a container; adding an EDTA/NaOH mixture to the container and subsequently adding at least one metal compound; and adding $Na_2SeO_3$ to the container to obtain the trace element solution. The method also comprises the step of adding $CrCl_3.6H_2O$ to the trace element solution.

Unfortunately the known methods do not always provide the ideal concentration requirements and ideal and required ratios and do not result in stable concentrations and trace element solutions. Also the known methods are difficult to process.

It is an object of the invention to suggest a trace element solution for overcoming these problems.

SUMMARY OF INVENTION

According to the invention, a trace element solution, comprises at least the following metals:
 (a) at least 65 mg/ml zinc derived directly and/or indirectly from mineral EDTA chelate(s);
 (b) at least 10 mg/ml manganese derived directly and/or indirectly from mineral EDTA chelate(s);
 (c) at least 15 mg/ml copper derived directly and/or indirectly from mineral EDTA chelate(s); and
 (d) at least 5 mg/ml selenium.

Also according to the invention, a trace element solution, comprises at least the following metals:
 (a) at least 65 mg/ml zinc derived directly and/or indirectly from ZN-EDTA and/or zinc oxide;
 (b) at least 10 mg/ml manganese derived directly and/or indirectly from Mn-EDTA and/or Mn carbonate;
 (c) at least 15 mg/ml copper derived directly and/or indirectly from Cu-EDTA and/or copper oxide and/or copper sulphate and/or copper carbonate; and
 (d) at least 5 mg/ml selenium derived from $Na_2SeO_4$ and/or $Na_2SeO_3$.

The mineral EDTA chelates may be derived directly and/or indirectly from Zinc oxide, manganese carbonate, copper carbonate, copper sulphate, copper oxide, EDTA and/or sodium hydroxide.

The trace element solution may additionally comprise iodine.

The trace element solution may additional comprise 50 mg/ml iodine.

The iodine may be derived from potassium iodide.
The ratio of zinc to manganese may be at least 6.5:1.
The ratio of zinc to copper may be at least 4:1.
The ratio of zinc to selenium may be at least 13:1.
The concentration of the metals (excluding iodine) may be at least 95 mg/ml.

In addition to the aforementioned materials, the trace element solution may also be prepared with the addition of water, chlorocresol and/or benzyl alcohol.

The pH of the trace element solution may be adjusted by means of 30% NaOH.

The solution may be an injectable trace element solution.

The solution may be visually stable.

The invention also extends to a method of preparing a trace element solution as described herein.

DESCRIPTION OF EXAMPLE

The invention will now be described by way of an example of a trace element solution in accordance with the invention.

The example relates to a trace element solution predominantly to be used for cattle and includes the mineral elements zinc, manganese, selenium and copper.

According to the invention, a trace element solution, comprises the following metals:
- (a) zinc directly and/or indirectly from mineral EDTA chelate(s);
- (b) manganese directly and/or indirectly from mineral EDTA chelate(s);
- (c) copper directly and/or indirectly from mineral EDTA chelate(s); and
- (d) selenium.

The trace element solution, comprises at least the following metals:
- (a) at least 65 mg/ml zinc derived directly and/or indirectly from ZN-EDTA and/or zinc oxide;
- (b) at least 10 mg/ml manganese derived directly and/or indirectly from Mn-EDTA and/or Mn carbonate;
- (c) at least 15 mg/ml copper derived directly and/or indirectly from Cu-EDTA and/or copper oxide and/or copper sulphate and/or copper carbonate; and
- (d) at least 5 mg/ml selenium derived from $Na_2SeO_4$ and/or $Na_2SeO_3$.

The trace element solution can additional comprise 50 mg/ml iodine.

The iodine is derived from potassium iodide.

The ratio of zinc to manganese is at least 6.5:1.

The ratio of zinc to copper is at least 4:1.

The ratio of zinc to selenium is at least 13:1.

The concentration of the metals (excluding iodine) is at least 95 mg/ml.

In addition to the aforementioned materials, the trace element solution is also be prepared with the addition of water, chlorocresol and/or benzyl alcohol.

The pH of the trace element solution is adjusted by means of 30% NaOH.

The solution can be an injectable trace element solution.

The solution is visually stable.

The mineral EDTA chelates can be derived directly and/or indirectly from Zinc oxide, manganese carbonate, copper carbonate, copper oxide, copper sulphate, EDTA and/or sodium hydroxide.

The invention also extends to a method of preparing a trace element solution as described herein.

EXAMPLE 1

Specifications

|  | g/L |
|---|---|
| Zinc | 65 |
| Manganese | 10 |
| Copper | 15 |
| Selenium | 5 |
| Iodine | 50 |

|  | g/L |
|---|---|
| (A) | |
| 1. Purified water | 637.255 |
| 2. Mn-EDTA (14.12%) | 70.83 |
| 3. Zn-EDTA (16.36%) | 397.31 |
| 4. Cu-EDTA (15.98%) | 93.89 |
| 5. Mix with silverson until solution is clear | |
| (B) | |
| 1. pH: | Record pH |
| 2. heat to 50° C. Add chlorocresol and mix until dissolved (±10 mins) | 1.1 |
| 3. pH: | Record pH |
| OR | |
| 1. pH: | record pH |
| 2. Add benzyl alcohol and mix until dissolved (±10 mins) | 10.46 |
| 3. pH: | Record pH |
| 4. Cool to <25° C. and add $Na_2SeO_4$ or $Na_2SeO_3$ | 11.96/10.95 |
| 5. pH: | |
| 6. Potassium Iodide | 65.407 |
| (C) | |
| 1. Adjust pH to 7/7.5/8 with 30% NaOH | |
| 2. SG: 1.275-1.35 | |
| 3. Filter solution | |

EXAMPLE 2

Specifications

|  | g/L |
|---|---|
| Zinc | 65 |
| Manganese | 10 |
| Copper | 15 |
| Selenium | 5 |
| (A) | |
| 6. Purified water | 637.255 |
| 7. Mn-EDTA (14.12%) | 70.83 |
| 8. Zn-EDTA (16.36%) | 397.31 |
| 9. Cu-EDTA (15.98%) | 93.89 |
| 10. Mix with silverson until solution is clear | |
| (B) | |
| 4. pH: | record |
| 5. Heat to 50° C. and add chlorocresol and mix until dissolved (±10 mins) | 1.1 |
| 6. pH: | Record |
| OR | |
| 7. pH: | |
| 8. Add benzyl alcohol and mix until dissolved (±10 mins) | 10.46 |
| 9. pH: | |
| 10. Cool to <25° C. and add $Na_2SeO_4$ or $Na_2SeO_3$ | 11.96/10.95 |
| 11. pH: | |
| (C) | |
| 1. Adjust pH to 7/7.5/8 with 30% NaOH | |
| 2. SG: 1.275-1.35 | |
| 3. Filter solution | |

EXAMPLE 3

Specifications

|  | g/L |
|---|---|
| Zinc | 70 |
| Manganese | 10 |
| Copper | 15 |
| Selenium | 5 |
| Iodine | 50 |
| (A) | |
| 11. Purified water | 637.255 |
| 12. Mn-EDTA (14.12%) | 70.83 |
| 13. Zn-EDTA (16.36%) | 427.87 |
| 14. Cu-EDTA (15.98%) | 93.89 |
| 15. Mix with silverson until solution is clear | |
| (B) | |
| 7. pH: | Record pH |
| 8. Heat to 50° C. and Add chlorocresol and mix until dissolved (±10 mins) | 1.1 |
| 9. pH: | Record pH |
| OR | |
| 12. pH : | |
| 13. Add benzyl alcohol and mix until dissolved (±10 mins) | 10.46 |
| 14. pH : | |
| 15. Cool to <20° C. and add Na$_2$SeO$_4$ or Na$_2$SeO$_3$ | 11.96/10.95 |
| 16. pH : | |
| 17. Potassium Iodide | 65.407 |
| (C) | |
| 1. Adjust pH to 7/7.5/8 with 30% NaOH | |
| 2. SG: 1.275-1.35 | |
| 3. Filter solution | |

EXAMPLE 4

|  | g/L |
|---|---|
| Zinc | 70 |
| Manganese | 10 |
| Copper | 15 |
| Selenium | 5 |
| (A) | |
| 16. Purified water | 637.255 |
| 17. Mn-EDTA (14.12%) | 70.83 |
| 18. Zn-EDTA (16.36%) | 427.87 |
| 19. Cu-EDTA (15.98%) | 93.89 |
| 20. Mix with silverson until solution is clear | |
| (B) | |
| 10. pH : | Record pH |
| 11. Heat to 50° C. and Add chlorocresol and mix until dissolved (±10 mins) | 1.1 |
| 12. pH : | Record pH |
| OR | |
| 18. pH : | |
| 19. Add benzyl alcohol and mix until dissolved (±10 mins) | 10.46 |
| 20. pH : | |
| 21. Cool to <20° C. and add Na$_2$SeO$_4$ or Na$_2$SeO$_3$ | 11.96/10.95 |
| 22. pH : | |
| (C) | |
| 1. Adjust pH to 7/7.5/8 with 30% NaOH | |
| 2. SG: 1.275-1.35 | |
| 3. Filter solution | |

The invention claimed is:

1. A trace element solution, which comprises at least the following metals:
   (a) zinc directly and/or indirectly from Zn-EDTA and/or Zn oxide, wherein zinc is present in at least 65 mg/ml zinc directly and/or indirectly from Zn-EDTA and/or Zn oxide;
   (b) manganese directly and/or indirectly from Mn-EDTA and/or manganese carbonate;
   (c) copper directly and/or indirectly from Cu-EDTA and/or copper oxide and/or copper sulphate, and/or copper carbonate; and
   (d) selenium derived directly and/or indirectly from Na$_2$SeO$_4$ and/or Na$_2$SeO$_3$,
   wherein the metals are present in a solution of water, chlorocresol and/or benzyl alcohol, at a concentration of metals of at least 95 mg/ml;
   wherein the pH of the trace element solution adjusted by means of 30% NaOH in an injectable trace element solution that is visually stable; and
   wherein a ratio of zinc to manganese is at least 6.5:1.

2. The trace element solution of claim 1, wherein manganese is present in at least 10 mg/ml manganese directly and/or indirectly from Mn-EDTA and/or manganese carbonate.

3. The trace element solution of claim 1, wherein copper is present in at least 15 mg/ml copper directly and/or indirectly from Cu-EDTA and/or copper oxide and/or copper sulphate, and/or copper carbonate.

4. The trace element solution of claim 1, wherein selenium is present in at least 5 mg/ml selenium derived directly and/or indirectly from Na$_2$SeO$_4$ and/or Na$_2$SeO$_3$.

5. The trace element solution of claim 1, wherein a ratio of zinc to copper is at least 4:1.

6. The trace element solution of claim 1, wherein a ratio of zinc to selenium is at least 13:1.

7. The trace element solution of claim 1, further comprises iodine.

8. The trace element solution of claim 7, wherein iodine is present in 50 mg/ml.

9. The trace element solution of claim 7, wherein the iodine is derived from potassium iodide.

* * * * *